(12) United States Patent
Wang et al.

(10) Patent No.: US 10,307,412 B2
(45) Date of Patent: Jun. 4, 2019

(54) QUINOLINE DERIVATIVE AGAINST NON-SMALL CELL LUNG CANCER

(71) Applicant: CHIA TAI TIANQING PHARMACEUTICAL GROUP CO., LTD., Jiangsu (CN)

(72) Inventors: Xunqiang Wang, Jiangsu (CN); Yadong Miu, Jiangsu (CN); Min Zhou, Jiangsu (CN); Shanchun Wang, Jiangsu (CN); Ling Yang, Jiangsu (CN); Wei Shi, Jiangsu (CN)

( * ) Notice: Subject to any disclaimer, the term of this patent is extended or adjusted under 35 U.S.C. 154(b) by 0 days.

(21) Appl. No.: 15/533,873

(22) PCT Filed: Dec. 9, 2015

(86) PCT No.: PCT/CN2015/096777
§ 371 (c)(1),
(2) Date: Jun. 7, 2017

(87) PCT Pub. No.: WO2016/091168
PCT Pub. Date: Jun. 16, 2016

(65) Prior Publication Data
US 2017/0304290 A1    Oct. 26, 2017

(30) Foreign Application Priority Data

Dec. 9, 2014   (CN) .......................... 2014 1 0749394

(51) Int. Cl.
| | |
|---|---|
| A61P 35/00 | (2006.01) |
| A61P 35/04 | (2006.01) |
| A61K 9/14 | (2006.01) |
| C07D 401/12 | (2006.01) |
| A61K 31/4035 | (2006.01) |
| A61K 31/4709 | (2006.01) |

(52) U.S. Cl.
CPC ............ *A61K 31/4709* (2013.01); *A61K 9/14* (2013.01); *A61K 31/4035* (2013.01); *A61P 35/00* (2018.01); *A61P 35/04* (2018.01); *C07D 401/12* (2013.01)

(58) Field of Classification Search
CPC .. A61K 31/4035; A61K 31/4709; A61K 9/14; C07D 401/12
USPC .................................. 514/1.1, 312; 546/159
See application file for complete search history.

(56) References Cited

U.S. PATENT DOCUMENTS

| | | | | |
|---|---|---|---|---|
| 8,148,532 | B2* | 4/2012 | Chen ................... | C07D 239/74 546/159 |
| 9,550,781 | B2* | 1/2017 | Xiao .................... | C07D 473/00 |
| 9,725,439 | B2* | 8/2017 | Xiao .................... | C07D 403/12 |
| 9,751,859 | B2* | 9/2017 | Chen .................... | C07D 401/12 |
| 2010/0105696 | A1 | 4/2010 | Garcia-Echevrria et al. | |
| 2016/0326138 | A1 | 11/2016 | Chen et al. | |
| 2017/0174687 | A1 | 6/2017 | Chen | |
| 2017/0182027 | A1* | 6/2017 | Wang ................ | A61K 31/4709 |
| 2017/0202828 | A1* | 7/2017 | Zhang ..................... | A61K 9/48 |
| 2018/0002311 | A1 | 1/2018 | Chen et al. | |

FOREIGN PATENT DOCUMENTS

| | | |
|---|---|---|
| CN | 101809012 | 8/2010 |
| CN | 102344438 | 2/2012 |
| WO | WO 2006/122806 | 11/2006 |
| WO | WO 2008/112407 | 9/2008 |
| WO | WO 2008/112408 | 9/2008 |
| WO | WO 2009/155527 | 12/2009 |
| WO | WO 2010/105761 | 9/2010 |
| WO | WO 2014/113616 | 7/2014 |

OTHER PUBLICATIONS

Sun et al., "Safety, pharmacokinetics, and antitumor properties of anlotinib, an oral multi-target tyrosine kinase inhibitor, in patients with advanced refractory solid tumors", 2016, Journal of Hematology & Oncology, 9:105; DOI 10.1186/s13045-016-0332-8. (Year: 2016).*
Han et al., "Anlotinib as a third-line therapy in patients with refractory advanced non-small-cell lung cancer: a multicentre, randomised phase II trial (ALTER0302)", 2018, British Journal of Cancer, 118(5), pp. 654-661. (Year: 2018).*
National Center for Biotechnology Information. PubChem Compound Database; CID=25017411, https://pubchem.ncbi.nlm.nih.gov/compound/25017411 (accessed Apr. 4, 2018). (Year: 2018).*
Bello, E. et al., E-3810 Is a Potent Dual Inhibitor of VEGFR and FGFR that Exerts Antitumor Activity in Multiple Preclinical Models, Cancer Research; 71(4), Feb. 15, 2011.
International Search Report on Patentability received in International Patent Application No. PCT/CN2015/096777, dated Mar. 2, 2016.
Moreno et al., Clin Transl Oncol (2010) 12:468-472.
Sala, F. et al., Development and validation of a high-performance liquid chromatography-tandem mass spectrometry method for the determination of the novel inhibitor of angiogenesis E-3810 in human plasma and its application in a clinical pharmacokinetic study, Journal of Mass Spectrometry, 2011, 46, pp. 1039-1045.

(Continued)

*Primary Examiner* — My-Chau T. Tran
(74) *Attorney, Agent, or Firm* — Knobbe, Martens, Olson & Bear, LLP

(57) ABSTRACT

The present application provides a quinoline derivative against non-small cell lung cancer. 1-[[[4-(4-fluoro-2-methyl)-1H-indol-5-yl)oxy-6-methoxyquinolin-7-yl]oxy]methyl]cyclopropylamine or a pharmaceutically acceptable salt thereof provided by the present application can be used for the treatment of non-small cell lung cancer, and relative to placebo, can significantly improve non-small cell lung cancer patients without progression of survival. 1-[[[4-(4-fluoro-2-methyl-1H-indol-5-yl)oxy-6-methoxyquinolin-7-yl]oxy]methyl]cyclopropylamine or a pharmaceutically acceptable salt thereof provided by the present application can be used for the treatment of lung adenocarcinoma, and relative to placebo, can significantly improve lung adenocarcinoma patients without progression of survival.

16 Claims, No Drawings

(56) References Cited

OTHER PUBLICATIONS

Traina et al.—Optimizing Chemotherapy Dose and Schedule by Norton-Simon Mathematical Modeling (cited in OA).
Zhou, Y. et al., AL3810, a multi-tyrosine kinase inhibitor, exhibits potent anti-angiogenic and ant-tumor activity via targeting VEGFR, FGFR, and PDGFR, Journal of Cellular and Molecular Medicine, vol. 16, No. 10, 2012 pp. 2321-2330.
Eskens et al, "Phase I Dose Escalation Study of Telatinib, a Tyrosine Kinase Inhibitor of Vascular Endothelial Growth Factor Receptor 2 and 3, Platelet-Derived Growth Factor Receptor β, and c-Kit, in Patients With Advanced or Metastatic Solid Tumors." Journal of Clinical Oncology (2009), vol. 27 (25), pp. 4169-4176.
XELODA® Prescribing Information; Genentech USA, Inc.,—Xeloda, Mar. 2015.

* cited by examiner

QUINOLINE DERIVATIVE AGAINST NON-SMALL CELL LUNG CANCER

CROSS-REFERENCES TO RELATED APPLICATIONS

Incorporation by Reference to any Priority Applications

This application is the U.S. National Phase of International Application PCT/CN2015/096777, filed Dec. 9, 2015, which claims priority and interest of China Patent Application No. 201410749394.0 filed with the China National Intellectual Property Office on Dec. 9, 2014, the disclosures of each of which are hereby incorporated by reference in their entireties.

TECHNICAL FIELD

The present application relates to the field of pharmaceutical technology, and the present application relates to the use of quinoline derivatives for antitumor purposes. Specifically, this application relates to the use of quinoline derivative in the treatment of non-small cell lung cancer (e.g., lung adenocarcinoma).

BACKGROUND TECHNIQUE

Cancer is a major public health problem in many parts of the world. Among them, lung cancer due to morbidity and mortality are high, becomes the whole one of the major causes of cancer death in the world, for non-small cell lung cancer (NSCLC), although platinum-containing chemotherapy can change the survival of advanced patients, but the prognosis of advanced non-small cell lung cancer is still very poor and 5-year survival rate is less than 10%. It is reported that further study of tumorigenesis and chemical resistance in lung cancer is required in order to increase survival (Jemal A et al., Cancer Statistics, CACancer. J. Clin., 56, 106-130, 2006). Based on cell morphology, adenocarcinoma is a common NSCLC group (Travis et al., Lung Cancer Principles and Practice, Lippincott-Raven, New York, 361-395, 1996). NSCLC's first-line chemotherapeutic regimen usually contains platinum-containing drugs, which points to that platinum-based drugs (cisplatin or carboplatin) are added with a second chemotherapeutic agent (Pacific paclitaxel, pemetrexed, gemcitabine, Vinorelbine, etc.) (Dadario et al., 2010; National Comprehensive Cancer Network Oncology Clinical Practice Guide, Non-small cell lung cancer, 2010 second edition). For the advanced non-small cell lung cancer, especially lung adenocarcinoma, although the driving gene targeted therapy has obtained a certain clinical efficacy, in the end there will be resistance which results in disease progression, and the treatment of lung adenocarcinoma with non-driven genes is still based on platinum-based chemotherapy. Therefore, non-small cell lung cancer and histological type of lung adenocarcinoma, still need to develop more drugs, in order to achieve better treatment, improve survival, to bring substantial benefits to patients.

AN OVERVIEW OF THE INVENTION

In one aspect, the present application provides a method of treating non-small cell lung cancer, comprising administering to a patient in need of treatment a therapeutically effective amount of a compound I having the following structural formula or a pharmaceutically acceptable salt thereof.

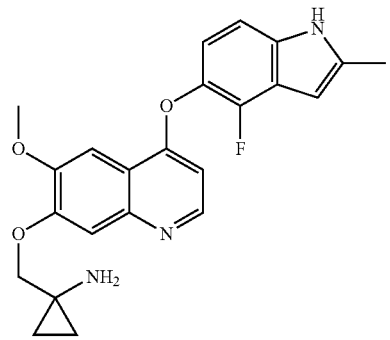 [SMILES: COc1cc2c(Oc3ccc4[nH]c(C)cc4c3F)ccnc2cc1OCC1(N)CC1]

Another aspect, the present application provides use of compound I having a structural formula as above or a pharmaceutically acceptable salt thereof, for the treatment of non-small cell lung cancer.

In yet another aspect, the present application provides a compound I or a pharmaceutical composition having the above structural formula for the treatment of non-small cell lung cancer, wherein the pharmaceutical composition comprises Compound I or a pharmaceutically acceptable salt thereof and at least one pharmaceutically acceptable carrier.

DETAILS OF THE INVENTION

In one aspect, the present application provides a method of treating non-small cell lung cancer, wherein the method comprises administering to a subject a therapeutically effective amount of a compound I having the following structural formula or a pharmaceutically acceptable salt thereof.

Compound I

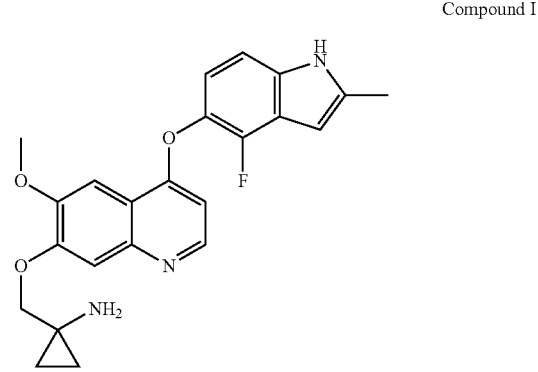 [SMILES: COc1cc2c(Oc3ccc4[nH]c(C)cc4c3F)ccnc2cc1OCC1(N)CC1]

Some embodiments of the present application provide a method of treating advanced non-small cell lung cancer and/or metastatic non-small cell lung, wherein the method comprises administering to a patient in need of treatment a therapeutically effective amount of Compound I or a pharmaceutically acceptable salt thereof.

Some embodiments of the present application provide a method of treating non-small cell lung cancer with EGFR mutations, wherein the method comprises administering to a patient in need of treatment a therapeutically effective amount of Compound I or a pharmaceutically acceptable salt thereof.

Some embodiments of the present application provide a method of treating lung adenocarcinoma, wherein the method comprises administering to a patient in need of treatment a therapeutically effective amount of Compound I or a pharmaceutically acceptable salt thereof.

Some embodiments of the present application provide a method of treating advanced lung adenocarcinoma and/or metastatic lung adenocarcinoma, wherein the method comprises administering to a patient in need of treatment a therapeutically effective amount of Compound I or a pharmaceutically acceptable salt thereof.

Some embodiments of the present application provide a method of treating lung adenocarcinoma with EGFR mutations negative, wherein the method comprises administering to a patient in need of treatment a therapeutically effective amount of Compound I or a pharmaceutically acceptable salt thereof.

The compound I may be administered in its free base form or in the form of its salt, hydrate and prodrug thereof, the prodrug is converted in vivo to the free base form of Compound I. For example, pharmaceutically acceptable salts of compound I, within the scope of this application, can be produced from different organic and inorganic acids according to methods known in the art.

In some embodiments, the compound I is administered in the form of a compound I hydrochloride. In some embodiments, compounds I is administered in the form of hydrochloride. In some embodiments, the compound I is administered in the form of dihydrochloride. In some embodiments, compounds I is administered in the form of crystals of compound I hydrochloride. In a particular embodiment, compounds I is administered in the form of the crystals of dihydrochloride.

Compound I has the chemical name 1-[[[4-(4-fluoro-2-methyl-1H-indol-5-yl) oxy-6-methoxyquinolin-7-yl]oxy] methyl] Cyclopropylamine, which has the following structural formula

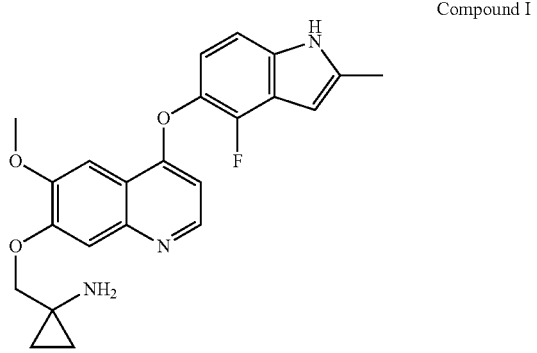 [SMILES: COc1cc2c(Oc3ccc4[nH]c(C)cc4c3F)ccnc2cc1OCC1(N)CC1]

Compound I

Compound I or a pharmaceutically acceptable salt thereof can be administered by a variety of routes including, but not limited to, oral, parenteral, intraperitoneal, intravenous, intraarterial, transdermal, sublingual, intramuscular, rectal, buccal, intranasal, inhalation, vagina, intraocular, topical, subcutaneous, adipose, intraarticular, intraperitoneal and intrathecal. In a particular implementation, it's administered by oral.

The amount of compound I or its pharmaceutically acceptable salt may be administered depending on the severity of the disease, the response to the disease, any treatment-related toxicity, patient's age and health status. In some embodiments, the daily dose of Compound I or a pharmaceutically acceptable salt is from 3 mg to 30 mg. In some embodiments, the daily dose of Compound I or a pharmaceutically acceptable salt is from 5 mg to 20 mg. In some embodiments, the daily dose of Compound I or a pharmaceutically acceptable salt is from 8 mg to 16 mg. In some embodiments, the daily dose of Compound I or a pharmaceutically acceptable salt is from 10 mg to 14 mg. In a particular embodiment, the daily dose of Compound I or a pharmaceutically acceptable salt is 8 mg. In a particular embodiment, the daily dose of Compound I or a pharmaceutically acceptable salt is 10 mg. In a particular embodiment, the daily dose of Compound I or a pharmaceutically acceptable salt is 12 mg.

Compound I or a pharmaceutically acceptable salt thereof may be administered once or more times daily. In some embodiments, the compound I or a pharmaceutically acceptable salt thereof is administered q.d. In one embodiment, the oral solid preparation is administered q.d.

In the above treatment method, the method of administration can be determined synthetically according to the activity of the drug, the toxicity, and the patient's tolerance. Preferably, Compound I or a pharmaceutically acceptable salt thereof is administered at intervals. The interval administration includes the dosing and withdrawal periods, and the compound I or a pharmaceutically acceptable salt thereof may be administered once or more times a day during the administration. For example, during the period of administration, Compound I or a pharmaceutically acceptable salt thereof is administered daily and then suspended for a period of time during the withdrawal period, followed by dosing period, and then withdrawal period, which can be repeated several times. The ratio of the number of days in the dosing period to the withdrawal period is 2:0.5 to 5, preferably 2:0.5 to 3, more preferably 2:0.5 to 2, more preferably 2:0.5 to 1.

In some embodiments, continuous medication lasts for 2 weeks, and then suspended medication lasts for 2 weeks. In some embodiments, the administration is once a day, continuous medication lasts for 14 days, and then suspended medication lasts for 14 days; followed by administration once a day for 14 days and then withdrawal for 14 days; Interval of administration that continuous medication lasts for 2 weeks, and then suspended medication lasts for 2 weeks can be repeated several times.

In some embodiments, continuous medication lasts for 2 weeks, and then suspended medication lasts for 1 week. In some embodiments, the administration is once a day, continuous medication lasts for 14 days, and then suspended medication lasts for 7 days; followed by administration once a day for 14 days and then withdrawal for 7 days; Interval of administration that continuous medication lasts for 2 weeks, and then suspended medication lasts for 1 week can be repeated several times.

In some embodiments, continuous medication lasts for 5 days and then suspended medication lasts for 2 days. In some embodiments, the administration is once a day, continuous medication lasts for 5 days, and then suspended medication lasts for 2 days; followed by administration once a day for 5 days and then withdrawal for 2 days; Interval of administration that continuous medication lasts for 5 days, and then suspended medication lasts for 2 days can be repeated several times.

In certain specific embodiments, the administration was oral once daily at a dose of 12 mg for 2 weeks and suspended for 1 week.

In another aspect, the present application provides use of compound I having a structural formula as below or a pharmaceutically acceptable salt thereof, for the treatment of non-small cell lung cancer.

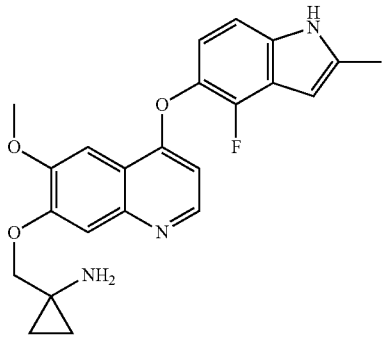 [SMILES: COc1cc2c(Oc3ccc4[nH]c(C)cc4c3F)ccnc2cc1OCC1(N)CC1]

Some embodiments of the present application provide use of compound I or a pharmaceutically acceptable salt thereof for the treatment of advanced non-small cell lung cancer and/or metastatic non-small cell lung cancer.

Some embodiments of the present application provide use of compound I or a pharmaceutically acceptable salt thereof for the treatment of EGFR mutant-negative non-small cell lung cancer.

Some embodiments of the present application provide use of compound I or a pharmaceutically acceptable salt thereof for the treatment of lung adenocarcinoma.

Some embodiments of the present application provide use of compound I or a pharmaceutically acceptable salt thereof for the treatment of EGFR mutant-negative lung adenocarcinoma.

Some embodiments of the present application provide use of compound I or a pharmaceutically acceptable salt thereof for the treatment of advanced lung adenocarcinoma and/or metastatic lung adenocarcinoma.

The compound I may be in its free base form or in the form of its salt, hydrate and prodrug thereof, the prodrug is converted in vivo to the free base form of Compound I. For example, pharmaceutically acceptable salts of compound I, within the scope of this application, can be produced from different organic and inorganic acids according to methods known in the art.

In some embodiments, the compound I or a pharmaceutically acceptable salt thereof is in the form of a compound I hydrochloride. In some embodiments, compounds I is in the form of hydrochloride. In some embodiments, the compound I is in the form of dihydrochloride. In some embodiments, compounds I is in the form of crystals of compound I hydrochloride. In a particular embodiment, compounds I is in the form of the crystals of dihydrochloride.

The amount of compound I or its pharmaceutically acceptable salt may be administered depending on the severity of the disease, the response to the disease, any treatment-related toxicity, patient's age and health status. In some embodiments, the daily dose of Compound I or a pharmaceutically acceptable salt is from 3 mg to 30 mg. In some embodiments, the daily dose of Compound I or a pharmaceutically acceptable salt is from 5 mg to 20 mg. In some embodiments, the daily dose of Compound I or a pharmaceutically acceptable salt is from 8 mg to 16 mg. In some embodiments, the daily dose of Compound I or a pharmaceutically acceptable salt is from 10 mg to 14 mg.

In yet another aspect, the present application provides a compound I or a pharmaceutical composition having the structural formula below for the treatment of non-small cell lung cancer, wherein the pharmaceutical composition comprises Compound I or a pharmaceutically acceptable salt thereof and at least one pharmaceutically acceptable carrier.

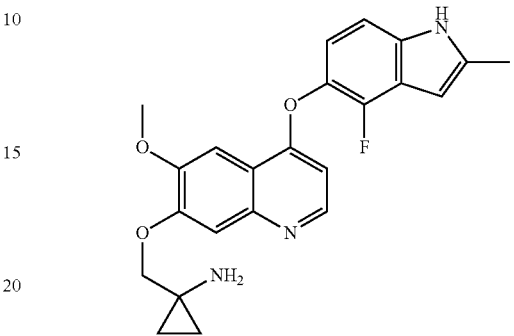

Some embodiments of the present application provide a compound I or a pharmaceutical composition for the treatment of advanced non-small cell lung cancer and/or metastatic non-small cell lung cancer, wherein the pharmaceutical composition comprises Compound I or a pharmaceutically acceptable salt thereof and at least one pharmaceutically acceptable carrier.

Some embodiments of the present application provide a compound I or a pharmaceutical composition for the treatment of EGFR mutant-negative non-small cell lung cancer, wherein the pharmaceutical composition comprises Compound I or a pharmaceutically acceptable salt thereof and at least one pharmaceutically acceptable carrier.

Some embodiments of the present application provide a compound I or a pharmaceutical composition for the treatment of lung adenocarcinoma, wherein the pharmaceutical composition comprises Compound I or a pharmaceutically acceptable salt thereof and at least one pharmaceutically acceptable carrier.

Some embodiments of the present application provide a compound I or a pharmaceutical composition for the treatment of advanced lung adenocarcinoma and/or metastatic lung adenocarcinoma, wherein the pharmaceutical composition comprises Compound I or a pharmaceutically acceptable salt thereof and at least one pharmaceutically acceptable carrier.

Some embodiments of the present application provide a compound I or a pharmaceutical composition for the treatment of EGFR mutant-negative lung adenocarcinoma, wherein the pharmaceutical composition comprises Compound I or a pharmaceutically acceptable salt thereof and at least one pharmaceutically acceptable carrier.

The compound I may be in its free base form or in the form of its salt, hydrate and prodrug thereof, the prodrug is converted in vivo to the free base form of Compound I. For example, pharmaceutically acceptable salts of compound I, within the scope of this application, can be produced from different organic and inorganic acids according to methods known in the art.

In some embodiments, the compound I or a pharmaceutically acceptable salt thereof is in the form of a compound I hydrochloride. In some embodiments, compounds I is in the form of hydrochloride. In some embodiments, the compound I is in the form of dihydrochloride. In some embodiments, compounds I is in the form of crystals of compound I hydrochloride. In a particular embodiment, compounds I is in the form of the crystals of dihydrochloride.

The amount of compound I or its pharmaceutically acceptable salt may be administered depending on the severity of the disease, the response to the disease, any treatment-related toxicity, patient's age and health status. In some embodiments, the pharmaceutical composition comprises from 3 mg to 30 mg of Compound I or a pharmaceutically acceptable salt thereof, based on unit dosage. In some embodiments, the above-mentioned pharmaceutical composition comprises from 5 mg to 20 mg of Compound I or a pharmaceutically acceptable salt thereof, based on unit dosage. In some embodiments, the above-mentioned pharmaceutical composition comprises from 8 mg to 16 mg of Compound I or a pharmaceutically acceptable salt thereof, based on unit dosage. In some embodiments, the above-mentioned pharmaceutical composition comprises from 10 mg to 14 mg of Compound I or a pharmaceutically acceptable salt thereof, based on unit dosage. In the present application, for example, for tablets or capsules, "they comprise 12 mg of Compound I, based on unit dosage" means that each tablet or each capsule contained in the final formulation contains 12 mg of Compound I.

In certain specific embodiments, wherein said pharmaceutical composition comprises 8, 10 or 12 mg of compound I or a pharmaceutically acceptable salt thereof, based on unit dosage.

In some embodiments, Compound I may be formulated for oral, parenteral, intraperitoneal, intravenous, intraarterial, transdermal, sublingual, intramuscular, rectal, buccal, intranasal, inhaled, vaginal, intraocular, locally administered, subcutaneous, Intraperitoneal, intraperitoneal and intrathecal preparations; preferably formulations suitable for oral administration, including tablets, capsules, powders, granules, agents, dropping pills, pastes, powders and the like, preferably tablets and capsules. Wherein the tablet may be an ordinary tablet, a dispersible tablet, an effervescent tablet, sustained release tablets, controlled release tablets or enteric tablets, and capsules can be ordinary capsules, sustained release capsules, controlled release capsules or enteric capsules. The said oral preparations can be prepared by conventional methods using pharmaceutically acceptable carriers known in the art. Pharmaceutically acceptable carriers include a filler, an absorbent, a wetting agent, a binder, a disintegrant, a lubricant, and the like. Fillers include starch, lactose, and mannitol, microcrystalline cellulose and the like; the absorbent includes calcium sulfate, calcium hydrogen phosphate, calcium carbonate and the like; the wetting agent includes water, ethanol and the like; adhesives include hydroxypropylmethylcellulose, povidone, microcrystalline cellulose and the like; disintegrating agents include croscarmellose sodium, crosslinked povidone, surfactants, low-substituted hydroxypropylcellulose and the like; lubricants include magnesium stearate, talc, polyethylene glycol, Sodium dodecyl sulfate, silica gel powder, talcum powder and the like. Pharmaceutical excipients also include colorants, sweeteners and the like.

The pharmaceutical compositions described may be formulated for oral, parenteral, intraperitoneal, intravenous, intraarterial, transdermal, sublingual, intramuscular, rectal, buccal, intranasal, inhaled, vaginal, intraocular, locally administered, subcutaneous, Intraperitoneal, intraperitoneal and intrathecal preparations; preferably formulations suitable for oral administration, including tablets, capsules, powders, granules, agents, dropping pills, pastes, powders and the like, preferably tablets and capsules. Wherein the tablet may be an ordinary tablet, a dispersible tablet, an effervescent tablet, sustained release tablets, controlled release tablets or enteric tablets, and capsules can be ordinary capsules, sustained release capsules, controlled release capsules or enteric capsules. The said oral preparations can be prepared by conventional methods using pharmaceutically acceptable carriers known in the art. Pharmaceutically acceptable carriers include a filler, an absorbent, a wetting agent, a binder, a disintegrant, a lubricant, and the like. Fillers include starch, lactose, and mannitol, microcrystalline cellulose and the like; the absorbent includes calcium sulfate, calcium hydrogen phosphate, calcium carbonate and the like; the wetting agent includes water, ethanol and the like; adhesives include hydroxypropylmethylcellulose, povidone, microcrystalline cellulose and the like; disintegrating agents include croscarmellose sodium, crosslinked povidone, surfactants, low-substituted hydroxypropylcellulose and the like; lubricants include magnesium stearate, talc, polyethylene glycol, Sodium dodecyl sulfate, silica gel powder, talcum powder and the like. Pharmaceutical excipients also include colorants, sweeteners and the like.

Preferably, Compound I or the above pharmaceutical composition is administered at intervals. The interval administration includes the dosing and withdrawal periods, and the compound I or the above pharmaceutical composition may be administered once or more times a day during the administration. For example, during the period of administration, Compound I or a pharmaceutically acceptable salt thereof is administered daily and then suspended for a period of time during the withdrawal period, followed by dosing period, and then withdrawal period, which can be repeated several times. The ratio of the number of days in the dosing period to the withdrawal period is 2:0.5 to 5, preferably 2:0.5 to 3, more preferably 2:0.5 to 2, more preferably 2:0.5 to 1.

In some embodiments, continuous medication lasts for 2 weeks, and then suspended medication lasts for 2 weeks. In some embodiments, the administration is once a day, continuous medication lasts for 14 days, and then suspended medication lasts for 14 days; followed by administration once a day for 14 days and then withdrawal for 14 days; Interval of administration that continuous medication lasts for 2 weeks, and then suspended medication lasts for 2 weeks can be repeated several times.

In some embodiments, continuous medication lasts for 2 weeks, and then suspended medication lasts for 1 week. In some embodiments, the administration is once a day, continuous medication lasts for 14 days, and then suspended medication lasts for 7 days; followed by administration once a day for 14 days and then withdrawal for 7 days; Interval of administration that continuous medication lasts for 2 weeks, and then suspended medication lasts for 1 week can be repeated several times.

In some embodiments, continuous medication lasts for 5 days and then suspended medication lasts for 2 days. In some embodiments, the administration is once a day, continuous medication lasts for 5 days, and then suspended medication lasts for 2 days; followed by administration once a day for 5 days and then withdrawal for 2 days; Interval of administration that continuous medication lasts for 5 days, and then suspended medication lasts for 2 days can be repeated several times.

In some embodiments, Compound I or the above pharmaceutical compositions may be administered once or more times daily. In some embodiments, Compound I or the above pharmaceutical composition is administered once a day. In some embodiments, the oral solid preparation is administered once a day.

In certain specific embodiments, the administration was oral once daily at a dose of 12 mg for 2 weeks and suspended for 1 week.

As used herein, "advanced" refers to staging of non-small cell lung cancer according to the degree of disease and concurrent disease, for example, it is according to AJCC cancer staging manual lung cancer staging system TNM classification of stage III-IV non-small cell lung cancer.

In some embodiments, advanced non-small cell lung cancer is stage IIIB-IV non-small cell lung cancer.

As used herein, "EGFR" refers to a epidermal growth factor receptor.

For those skilled in the art, "EGFR mutations negative" generally refers to that no EGFR gene mutation was detected according to a gene detection method commonly used in clinical diagnosis. EGFR mutations can be detected in a variety of ways, DNA mutation detection is detected EGFR status of the preferred method, a variety of DNA mutation detection can be used to detect EGFR mutation state of tumor cell. For non-small cell lung cancer patients, the most common EGFR mutations are exon 19 deletions and exon 21 mutations, and exons 18-21 (Or only exons 19 and 21) direct DNA sequencing is a reasonable choice.

As used herein, unless otherwise indicated, the dosages and ranges provided herein are calculated based on the molecular weight of the compound I free base form.

In this context, the amount of compound I administered may vary depending on the severity of the disease, the response to the disease, any treatment-related toxicity, the age and health status of the patient. The period of administration can be determined based on the activity of the drug, the toxicity and the patient's tolerance.

Unless otherwise indicated, for the purposes of this application, the following terms used in this specification and in the claims should have the following meaning.

"Patient" refers to a mammal, preferably a human.

"Pharmaceutically acceptable" refers to the use thereof for the preparation of a pharmaceutical composition which is generally safe, non-toxic and is neither biologically or otherwise undesirable and includes that it's acceptable for the use of human drugs.

"Pharmaceutically acceptable salts" include, but are not limited to, salts with inorganic acids such as hydrochloric acid, hydrobromic acid, sulfuric acid, nitric acid, phosphoric acid, etc;

Or an organic acid such as acetic acid, trifluoroacetic acid, propionic acid, caproic acid, heptanoic acid, cyclopentanepropionic acid, ethyl alkyd, Pyruvate, Lactic Acid, Malonic Acid, Succinic Acid, Malic Acid, Maleic Acid, Fumaric Acid, Tartaric Acid, Citric Acid, Benzyl Acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, P-toluenesulfonic acid, 3-phenylpropionic acid, trimethylacetic acid, t-butylacetic acid, dodecylsulfuric acid, gluconic acid, glutamic acid, naphthoic acid, salicylic acid, stearic acid and the like.

"Therapeutically effective amount" means that the compound is administered to a human being for the treatment of the disease sufficient to achieve the control of the disease.

"Treatment" means any administration of a therapeutically effective amount of a compound and includes:

(1) Inhibiting the disease in the human body that is experiencing or exhibiting the pathology or symptoms of the disease (i.e., preventing the further development of pathology and/or symptoms), or (2) Improving the disease in the human body that is experiencing or exhibiting the pathology or symptoms of the disease (i.e., reversing the pathology and/or symptoms)

In this paper, progression-free survival P25 refers to the time that 75% of the patients who participated in the disease had no progress in disease; Progressive survival P50 refers to the time that 50% of the patients who participated in the disease had no progress in disease; Progression-free survival P75 refers to the time that 25% of the patients who participated in the disease had no progress in disease; the progression-free survival was the mean value of the progression-free survival of the patient who participated in the results of statistics.

The following specific examples only illustrate the technical solutions of the present invention, which scope is not limited to the described embodiments.

Example 1

1-[[[4-(4-fluoro-2-methyl-1H-indol-5-yl)oxy-6-methoxyquinolin-7-yl]oxy]methyl]cyclopropylamine dihydrochloride

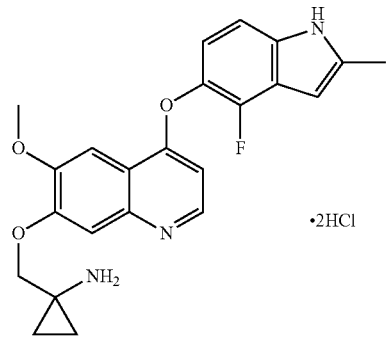 [SMILES: COc1cc2c(Oc3ccc4[nH]c(C)cc4c3F)ccnc2cc1OCC1(N)CC1]

1-[[[4-(4-fluoro-2-methyl-1H-indol-5-yl)oxy-6-methoxyquinolin-7-yl]oxy]methyl]cyclopropylamine was prepared by the method of Example 24 in WO2008112407, and then referring to the preparation method in "Examples of salt formation" of the description, the title compound was prepared.

Example 2

The Capsules containing 1-[[[4-(4-fluoro-2-methyl-1H-indol-5-yl)oxy-6-methoxy-quinolin-7-yl]oxy]methyl]cyclopropylamine dihydrochloride (dihydrochloride of compound I).

| Ingredients | amount (1000 capsules) |
|---|---|
| dihydrochloride of compound I | 14.16 g (equivalent to 12 g of compound I) |
| Mannitol | 89 g |
| Microcrystalline cellulose | 138.4 g |
| Hydroxypropyl cellulose | 5.9 g |
| Magnesium stearate | 0.99 g |

The dihydrochloride of the compound I was pulverized and sifted with a 80 mesh sieve, and then mixed with mannitol and hydroxypropyl cellulose uniformly, the prescribed amount of microcrystalline cellulose was added subsequently, mixed evenly and sifted with a 0.8 mm sieve;

finally the prescribed amount of magnesium stearate was added and mixed evenly, the obtained mixture was filled into capsules.

Example 3

Randomized, double-blind, placebo-controlled trials were performed in patients with measurable lesions which were pathologically diagnosedas non-small cell lung cancer, who had received second-line or higher-line therapy, or those who were intolerable to aforementioned treatment, and who had been treated with other cytotoxic drugs, radiotherapy or surgery for more than four weeks. In this study, efficacy of the capsules of dihydrochloride of compound I was initially evaluated against placebo in the treatment of patients with non-small cell lung cancer. The primary outcome of the evaluation was progression-free survival (PFS). 117 patients with non-small cell lung cancer enrolled in this study, whose age was between 18-70. Among them, 57 patients were randomized into placebo group and 60 patients randomized into dihydrochloride of compound I group.

The above-mentioned eligible non-small cell lung cancer patients were treated with dihydrochloride of compound I/placebo for clinical trials. They were administered 12 mg/0 mg of compound I/placebo individually once daily for consecutive two weeks followed by one-week rest from administration, namely the period of a cycle regimen was three weeks (21 days), those who were ineligible for continuous therapy or whose disease were progressive disease (PD) according to the reassessment were excluded from the medication.

Results: A total of 117 patients with non-small cell lung cancer were enrolled in the study, including 57 patients randomized into placebo group and 60 patients randomized into dihydrochloride of compound I group. 43 patients in placebo group and 30 patients in dihydrochloride of compound I group were involved in data statistics, the remaining patients who dropped out or excluded from the study or those were still in follow-up were not included in the statistics. The results were shown in the table below:

| Stratification factor | Group | Number of patients | progression-free survival (PFS, month) | | | |
|---|---|---|---|---|---|---|
| | | | P25 | P50 | P75 | Mean |
| age > 60 | Placebo | 11 | 0.67 | 1.38 | 4.17 | 2.48 |
| | dihydrochloride of compound I | 8 | 2.83 | 6.40 | 8.30 | 5.84 |
| age ≤ 60 | Placebo | 32 | 0.67 | 0.83 | 2.73 | 1.91 |
| | dihydrochloride of compound I | 24 | 2.77 | 4.30 | 6.17 | 4.48 |

The above results showed that dihydrochloride of compound I could significantly prolong progression-free survival in patients with non-small cell lung cancer.

Example 4

Randomized, double-blind, placebo-controlled trials were performed in patients with measurable lesions which were pathologically diagnosedas lung adenocarcinoma, who had received second-line or higher-line therapy, or those who were intolerable to the aforementioned treatment, and who had been treated with other cytotoxic drugs, radiotherapy or surgery for more than four weeks. In this study, efficacy of the capsules of dihydrochloride of compound I was initially evaluated against placebo in the treatment of patients with lung adenocarcinoma. The primary outcome of the evaluation was progression-free survival (PFS). 104 patients with lung adenocarcinoma enrolled in this study, whose age was between 18-70. Among them, 50 patients were randomized into placebo group and 54 patients randomized into dihydrochloride of compound I group.

The above-mentioned eligible lung adenocarcinoma patients were treated with dihydrochloride of compound I/placebo for clinical trials. They were administered 12 mg/0 mg of compound I/placebo individually once daily for consecutive two weeks followed by one-week rest from administration, namely the period of a cycle regimen was three weeks (21 days), those who were ineligible for continuous therapy or whose disease were progressive disease (PD) according to the reassessment were excluded from the medication.

Results: A total of 104 patients with lung adenocarcinoma were enrolled in the study, including 50 patients randomized into placebo group and 54 patients randomized into dihydrochloride of compound I group. 37 patients in placebo group and 30 patients in dihydrochloride of compound I group were involved in data statistics, the remaining patients who dropped out or excluded from the study or those were still in follow-up were not included in the statistics. The results were shown in the table below:

| Group | Number of patients | progression-free survival (PFS, month) | | | |
|---|---|---|---|---|---|
| | | P25 | P50 | P75 | Mean |
| Placebo | 37 | 0.67 | 1.23 | 2.87 | 2.18 |
| dihydrochloride of compound I | 30 | 2.77 | 4.33 | 6.87 | 4.77 |

The above results showed that dihydrochloride of compound I could significantly prolong progression-free survival in patients with lung adenocarcinoma.

Example 5

A) Medical History

Female, 45 years old, born on Jan. 11, 1968, with hyperlipidemia history while no smoking history. On Jan. 6, 2011, Bronchial brush biopsy showed high probability of non-small cell carcinoma, adenocarcinoma, combined with imaging findings, achieved the clinical diagnosis: right lower lung adenocarcinoma, right pleural metastasis, bilateral lung metastasis, mediastinal lymph node metastasis, and brain metastasis (T4N2M1b, stage IV). From Jan. 20, 2011 to Apr. 1, 2011, pemetrexed/cisplatin combination regimen was given for 4 treatment cycles, the best overall response was SD (stable disease). Erlotinib was given from May 5, 2011 to May 30, 2012, the best overall response was PR (partial response). From Jun. 4, 2012 to Aug. 18, 2012, docetaxel/neda-platin combination regimen was repeated for 4 cycles, the best overall response was SD (stable disease). Erlotinib was given from Dec. 3, 2012 to Aug. 3, 2013, the best overall response was SD (stable disease). From May 13, 2013 to Aug. 10, 2013, gemcitabine/carboplatin combination regimen was repeated for 5 cycles the best overall response was PR (partial response).

From Sep. 3, 2013, the capsule of dihydrochloride of compound I was taken orally at 12 mg once daily with repeated treatment cycles (treatment given for consecutive two weeks followed by one week of rest is one treatment cycle).

B) Assessment of Treatment Response and Toxicities

Treatment toxicities were assessed at 4-week follow-up, and the number of blood cells and blood chemistry were analyzed every two or three weeks, treatment response was assessed based on CT scan as well.

C) CT Scan Results

After treatment with dihydrochloride of compound I for 6 weeks, the sum of the longest diameter of the two measurable lesions was reduced from 45.7 mm to 31.43 mm (31.22% reduction), then reduced to 26 mm (43.1% reduction) when consecutively treated for ten treatment cycles (210 days), evaluation of the best overall response was PR (partial response).

D) Tolerance

In general, treatment with dihydrochloride of compound I was well tolerated, and blood routine examinations including the number of blood cells were not significantly altered.

Example 6

A) Medical History

A 67-year-old retired woman, smoking for 30 years (20 cigarettes/day), underwent thyroid adenoma resection 10 years ago. Previous bronchial brush biopsy showed non-small cell carcinoma, with high probability of adenocarcinoma, combined with imaging findings, achieved the clinical diagnosis: left upper lobe lung adenocarcinoma, bilateral lung metastasis, mediastinal lymph node metastasis, bilateral supraclavicular lymph node metastasis (T4N3M1a, stage IV), accompanied by multiple lacunar infarction, pericardial effusion, cholangiolithiasis and other diseases. From Aug. 1, 2013 to Sep. 1, 2013, a treatment cycle of TP regimen (paclitaxel/cisplatin) was given, while the outcome was unsatisfactory, chemotherapy regimen was changed subsequently. From Dec. 26, 2013 to Jan. 15, 2014, the GP regimen (gemcitabine/cisplatin) was given for one treatment cycle still with unsatisfactory outcome. On Jan. 20, 2014, Icotinib Hydrochloride Tablets 125 mg p.o. tid. were given with unknown outcome. On Feb. 27, 2014, CT scan showed that the several lesions existed in parts of body including bilateral lung, hilum of left lung lymph node, bilateral supraclavicular lymph node, and mediastinal lymph node, in which the longest diameter of the lesion in anterior segment of the left upper lobe lung was 37 mm, and the shortest diameter of the lesion in mediastinal lymph node was 21 mm. Tumor marker tests showed that the level of CEA was up to 107.41 ng/mL, which is not within the normal range.

From Feb. 28, 2014, the capsule of dihydrochloride of compound I was taken orally at 12 mg once daily with repeated treatment cycles (treatment given for consecutive two weeks followed by one week of rest is one treatment cycle).

B) CT Scan Results

After treatment with dihydrochloride of compound I, the sum of the longest diameter of the target lesions reduced considerably. Before undergoing the therapy, the sum of the diameter of two measurable target lesions was 58 mm (the anterior segment of left upper lobe lung 37 mm, the mediastinal lymph node 21 mm), and reduced to 36 mm after three-week administration, i.e., reduced by 37.9% (the anterior segment of left upper lobe lung 18 mm, the mediastinal lymph node 18 mm); then reduced to 29 mm when administration was given for six weeks, i.e., reduced by 50% (the anterior segment of left upper lobe lung 14 mm, the mediastinal lymph node 15 mm); and reduced to 26 mm after nine-week administration, i.e., reduced by 55.2% (anterior segment of left upper lobe lung 10 mm, the mediastinal lymph node 16 mm); then remained 26 mm when administration was given for twelve weeks, i.e., reduced by 55.2% (anterior segment of left upper lobe lung 10 mm and the mediastinal lymph node 16 mm); and reduced to 25 mm, i.e., reduced by 56.9% after 15-week administration (anterior segment of left upper lobe lung 10 mm, the mediastinal lymph node lesions 15 mm). progression of non-target lesions and new lesions were not observed. Until Dec. 4, 2014, dihydrochloride of compound I had been given for 279 days, and the treatment continued during the 14th treatment cycle, while sustained response against tumor and good clinical performance of the therapy was observed.

C) Tolerance

Treatment with dihydrochloride of compound I was generally well tolerated. Blood changes were not significant. There was no heart toxicity related to the drug during treatment.

Example 7

On Jun. 2, 2014, a 62-year-old female patient was found left lung cancer, lung metastasis, double hilar and mediastinum, right supraclavicular lymph node metastasis by CT examination, and ECT suggested bone metastases, cranial MRI suggested left frontal lobe transfer. She was diagnosed as non-small cell lung cancer by CT-guided lung puncture. EML4-ALK fusion gene had no mutation, EGFR gene had no mutation by gene detection.

From Jun. 9, 2014 to Sep. 25, 2014, the patient was treated with cisplatin and pemetrexed chemotherapy for 6 cycles, and the best efficacy was PR. During the treatment the patient had II degree gastrointestinal reactions, no bone marrow suppression. From Oct. 17, 2014 to Nov. 1, 2014 at the time of discharge, the patient was treated with Ti guio capsules for 2 weeks, and had cough relief, mild chest tightness. On Jan. 27, 2015 disease was found progression by check. From Jan. 31, 2015 to Jun. 21, 2015, the patient was treated with Icotinib combined with docetaxel chemotherapy for 6 cycles, and the best efficacy was SD. On Jul. 8, 2015, the patient participated in the clinical study of dihydrochloride of compound I capsules, and the same day began the dihydrochloride of compound I capsule treatment that one cycle plan was 12 mg dose once, q.d., and continuous medication for 2 weeks, and then suspended medication for 1 week.

On Jul. 29, 2015 patients received treatment for 1 cycle, and enhanced CT suggested left upper lobe of the lung with obstructive inflammation, double lung shift, the gap between the lower lobe of the lungs thickening, left hilar and mediastinal lymph node metastasis, right supraclavicular lymph nodes, and the double lateral pleural metastasis was likely, and part turned better, and part didn't change significantly. Evaluation of the best efficacy has reached PR according to RECIST1.1.

On Aug. 20, 2015 Patients' head enhancement CT suggested that the left temporal lobe nodules were slightly smaller than baseline.

On Nov. 12, 2015 enhanced CT suggested that the condition has been controlled, and the efficacy was still PR. Until application date, the patient could tolerate adverse reactions and continued to receive treatment.

Example 8

March 2013, a 62-year-old male was diagnosed as non-small cell lung cancer squamous cell carcinoma by CT-guided lung puncture and cranial MRI suggested left frontal lobe transfer. EML4-ALK fusion gene had no mutation, EGFR gene had no mutation by gene detection.

From Mar. 26, 2013 to Jun. 5, 2013, the patient was treated with cisplatin and gemcitabine chemotherapy for 4 cycles, and the best efficacy was SD. After the end of the chemotherapy, he was treated with the local radiotherapy of the lung for 1 cycle, during which the adverse reactions was light. From Sep. 9, 2013 to Oct. 6, 2013, the patient was treated with cisplatin and gemcitabine chemotherapy for 2 cycles. December 2013, disease was found progression by review of CT. From Mar. 24, 2014, the patient was treated with docetaxel chemotherapy for 1 cycle. After chemotherapy, bone marrow suppression, oral infection, pneumonia appeared, and the condition improved after symptomatic treatment. On Dec. 10, 2014, review CT suggested that: 1 Right upper hind plate soft tissue shadow increased than before; 2. Double lungs had multiple pulmonary bullae, which changed little than before; 3. Double lungs had inflammation, the scope of which was smaller than before; 4. Left clavicle, mediastinal and right hilar had multiple lymph nodes, which were slightly larger than before. From Jan. 7, 2015 to Jan. 29, 2015, Gemcitabine and nedaplatin (NDP) were given and grade III bone marrow suppression appeared after chemotherapy, which recovered after Rise white was given. On Mar. 4, 2015 review CT suggested that right lung mass increased than before. On Mar. 6, 2015, the patient was treated with oral Tiggio treatment. On May 27, 2015 Review CT suggested progress. On Jun. 2, 2015 pathology diagnosis suggested (right lung) poorly differentiated carcinoma after right lung squamous cell carcinoma radiotherapy and chemotherapy.

From Jun. 4, 2015, the patient received dihydrochloride of compound I capsule treatment that one cycle plan was 12 mg dose once, q.d., and continuous medication for 2 weeks, and then suspended medication for 1 week. On Jun. 25, 2015 patient was treated for 1 cycle, and enhanced CT suggested right hilar soft tissue density lumps, which were slightly smaller than before; Left clavicle, mediastinal and right hilar had multiple lymph nodes; Double lungs had inflammation, which changed little than before; Double lungs had multiple pulmonary bullae, which changed little than before; Evaluation of efficacy has reached SD according to RECIST1.1, and the total target lesions was 66 mm, which was reduced by 10 mm than the baseline On Jul. 15, 2015 patient's enhanced CT suggested right hilar soft tissue density lumps, which were slightly smaller than before. Target lesion sum was 63 mm; On Sep. 8, 2015, enhanced CT suggested lesions were further reduced, and target lesion sum was 57 mm; On Oct. 16, 2015 enhanced CT suggested lesions were reduced, the target lesion sum was 56 mm, which changed little than before; Until application date, the patient could tolerate adverse reactions and continued to receive treatment.

The invention claimed is:

1. A method of treating advanced and/or metastatic non-small cell lung cancer, the method comprising:
orally administering to a human patient in need of treatment who has received a second-line or a higher-line therapy a therapeutically effective amount of compound I having the following structural formula or a pharmaceutically acceptable salt thereof,

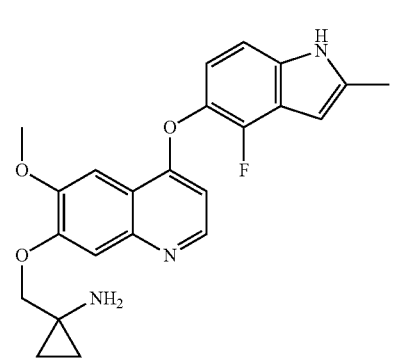 [SMILES: COc1cc2c(Oc3ccc4[nH]c(C)cc4c3F)ccnc2cc1OCC1(N)CC1]

Compound I wherein Compound I or the pharmaceutically acceptable salt thereof is administered at intervals and the ratio of the number of days in the dosing period to the withdrawal period is 2:0.5 to 2.

2. The method according to claim 1, wherein the non-small cell lung cancer is EGFR mutant-negative non-small cell lung cancer.

3. The method according to claim 1, wherein the non-small cell lung cancer is lung adenocarcinoma.

4. The method according to claim 1, wherein the non-small cell lung cancer is EGFR mutant-negative lung adenocarcinoma.

5. The method according to claim 1, wherein the said compound I or the pharmaceutically acceptable salt thereof is a hydrochloride of compound I.

6. The method according to claim 1, wherein compound I or the pharmaceutically acceptable salt thereof is administered for 2 weeks and then suspended for 1 week.

7. The method according to claim 6, wherein the daily dose of Compound I or the pharmaceutically acceptable salt is from 3 mg to 30 mg.

8. The method according to claim 1, wherein compound I or the pharmaceutically acceptable salt thereof is administered once per day with an oral solid preparation.

9. The method according to claim 1, wherein a dose of 8 mg, 10 mg, or 12 mg of compound I or the pharmaceutically acceptable salt thereof is administered once per day for 2 weeks and then suspended for 1 week.

10. A method of treating advanced and/or metastatic non-small cell lung cancer, the method comprising:
orally administering to a human patient having non-small cell lung cancer who has received a second-line or a higher-line therapy a pharmaceutical composition comprising a therapeutically effective amount of a compound having the structural formula of Compound I and at least one pharmaceutically acceptable carrier,

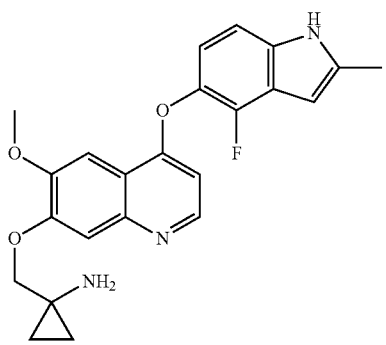

Compound I wherein the pharmaceutical composition is administered at intervals, the ratio of the number of days in the dosing period to the withdrawal period is 2:0.5 to 2.

11. The method according to claim 10, wherein non-small cell lung cancer is EGFR mutation negative non-small cell lung cancer.

12. The method according to claim 10, wherein the pharmaceutical composition is a tablet, a capsule, a powder, a granule, or a dropping pill.

13. The method according to claim 1, wherein compound I or the pharmaceutically acceptable salt thereof comprises a monohydrochloride salt of compound I.

14. The method according to claim 1, wherein compound I or the pharmaceutically acceptable salt thereof comprises a dihydrochloride salt of compound I.

15. The method according to claim 10, wherein the pharmaceutical composition is administered for 2 weeks and then suspended for 1 week.

16. The method according to claim 10, wherein the pharmaceutical composition is administered for 2 weeks once per day and then suspended for 1 week.

* * * * *